US006461853B1

United States Patent
Zhu

(10) Patent No.: US 6,461,853 B1
(45) Date of Patent: Oct. 8, 2002

(54) METHOD FOR SURFACE CULTURE OF MICROORGANISMS AND CELLS IN FLEXIBLE CULTURE BAGS

(76) Inventor: Hong Zhu, 1650 Tasco Close, Victoria, B.C. (CA), V8N 5P2

(*) Notice: Subject to any disclaimer, the term of this patent is extended or adjusted under 35 U.S.C. 154(b) by 0 days.

(21) Appl. No.: 09/858,451

(22) Filed: May 17, 2001

(51) Int. Cl.⁷ .................................................. C12N 1/00
(52) U.S. Cl. ...................................................... 435/243
(58) Field of Search ......................................... 435/243

(56) References Cited

U.S. PATENT DOCUMENTS

| | | |
|---|---|---|
| 4,063,383 A | 12/1977 | Green |
| 4,311,477 A | 1/1982 | Kitamura et al. |
| 4,939,151 A | 7/1990 | Bacehowski et al. |
| 4,977,702 A | 12/1990 | Fortin et al. |
| 5,225,346 A | 11/1993 | Matsumiya et al. |
| 5,659,997 A | 8/1997 | Sprehe et al. |
| 5,686,304 A | 11/1997 | Cohner |
| 5,736,398 A | 4/1998 | Giambernardi et al. |
| 6,190,913 B1 | 2/2001 | Singh |

OTHER PUBLICATIONS

Sikyta, Progress in Industrial Microbiology. 1995 vol. 31 pp. 177–185.
Kybal and Vlcek, A Simple Device for Stationary Cultivation of Microorganisms. Biotechnology and Bioengineering 1976, 18: 1713–1718.
Kybal and Sikyta. A Device for Cultivation of Plant and Animal Cells. Biotechnology Letters. 1985. 7: 467–470.

*Primary Examiner*—Remy Yucel
*Assistant Examiner*—Bronwen M. Loeb

(57) ABSTRACT

A method of using flexible bags for surface culture of microorganisms and cells on a stationary interface between a gaseous phase and a liquid medium and the devices upon which the method are practiced are disclosed. A flexible culture bag is first filled with a liquid growth medium, a sample inoculum, and a predetermined amount of air to create a headspace. The bag is then sealed and placed on a stationary platform, and mounted with an external self-support device on the top web of the bag. The external support device holds the top web of the bag in a fixed position and, thus, prevents the bag from deflating so that a stationary interface between the headspace and the liquid medium in the bag is maintained throughout the cultivation period.

18 Claims, 4 Drawing Sheets

FIG. 1. Top view
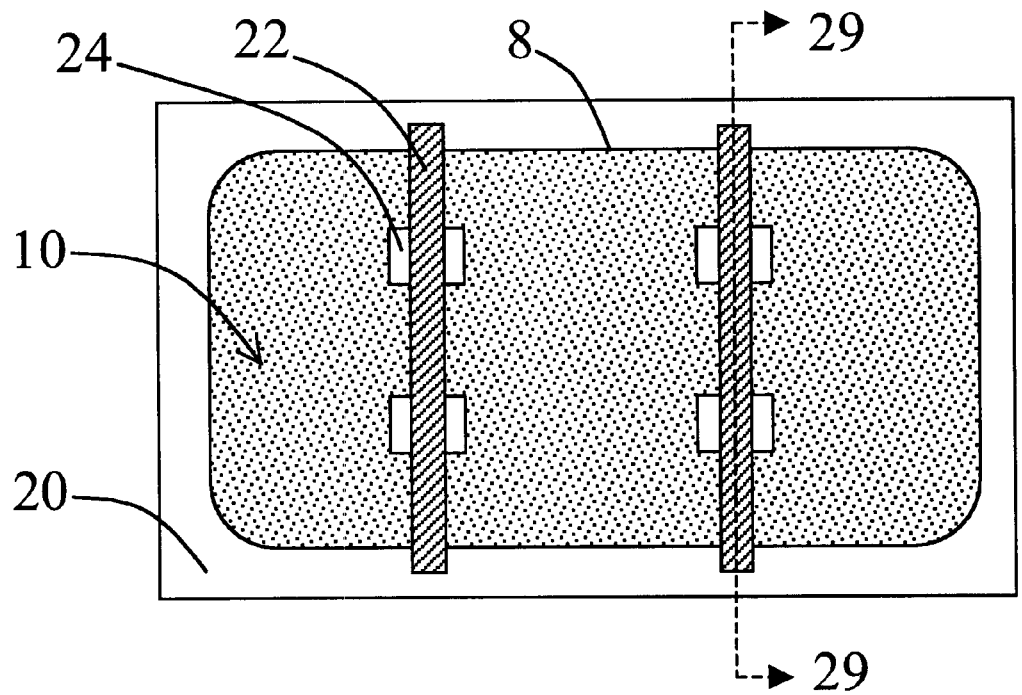
FIG. 2. Cross-sectional view
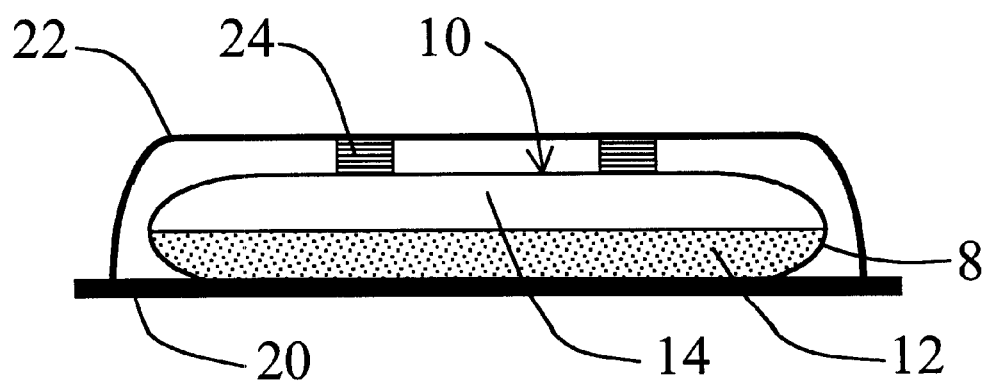

FIG. 3. Top view
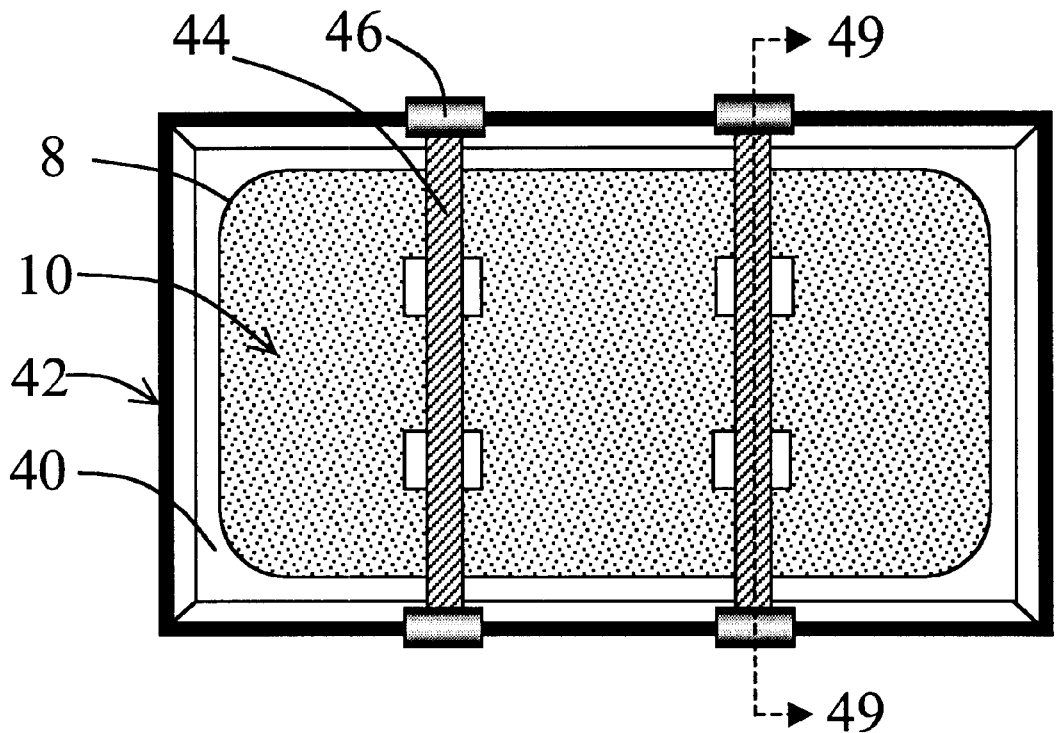
FIG. 4. Cross-sectional view
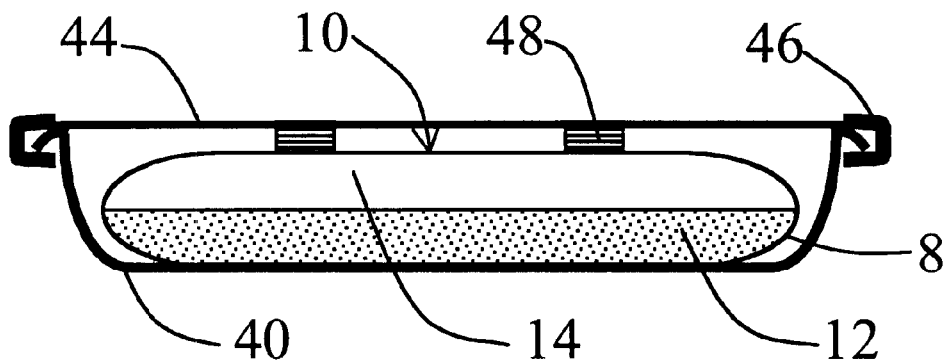

FIG. 5. Top view
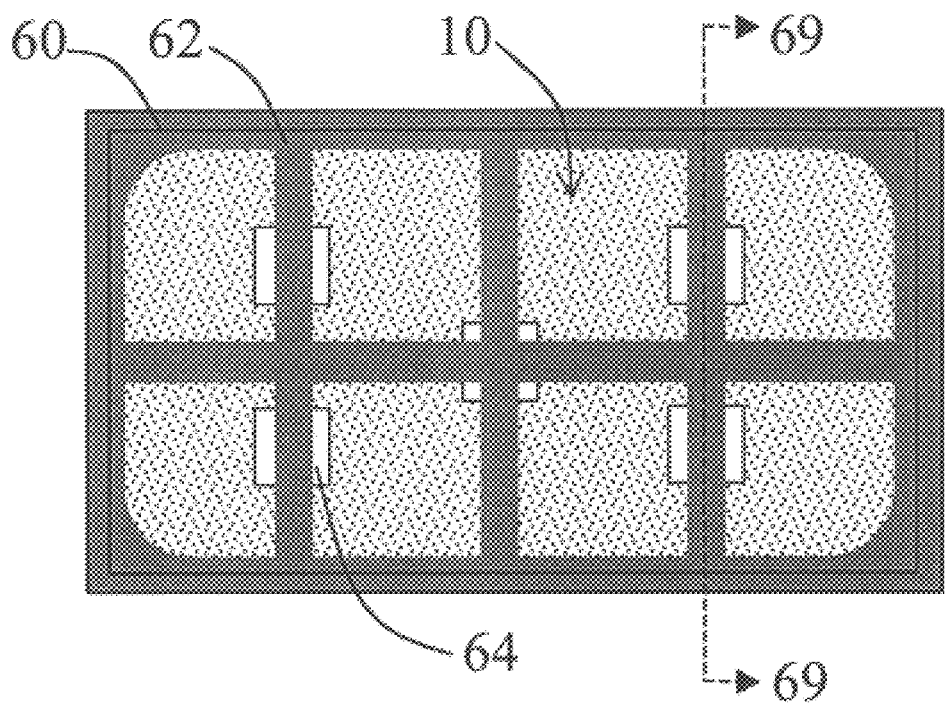
FIG. 6. Cross-sectional view
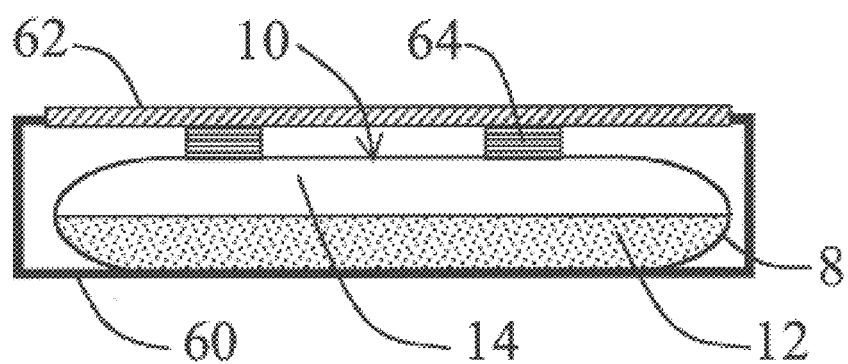

METHOD FOR SURFACE CULTURE OF MICROORGANISMS AND CELLS IN FLEXIBLE CULTURE BAGS

CROSS-REFERENCE TO RELATED APPLICATIONS

Not Applicable.

STATEMENT REGARDING FEDERALLY SPONSORED RESEARCH OR DEVELOPMENT

Not Applicable.

REFERENCE TO A MICROFICHE APPENDIX

Not Applicable.

BACKGROUND OF THE INVENTION

1. Field of Invention

This invention is related to a method for surface culture of microorganisms and cells in flexible culture bags.

2. Prior Art

Surface culture is one of the most common microbiological techniques for growing microorganisms and cells. By definition, surface culture refers to techniques and. processes where microorganisms or cells are grown on a stationary interface between a liquid phase a gaseous phase. A typical example of surface culture is growing Penicillum species in a petri dish filled with a thin layer of liquid medium, where the microorganisms is grown on the surface of the liquid medium that exposes to air.

Most of microorganisms are readily grown and differentiated on the stationary interface. In some cases, surface culture is the only means to culture certain microorganisms or to produce valuable products from certain microorganisms. For this reason and its simplicity, surface culture has been widely used in laboratories and to some degree in industrial fermentation, such as fermented food and antibiotics production.

In laboratory, surface culture is conventionally carried out in petri dishes, flasks or bottles. In industrial scales, surface culture is conventionally carried out in large pans or trays made of aluminum, stainless steel or rigid plastics as described by Sikyta (Progress in Industrial Microbiology, Vol. 31, pp. 177–185, 1995). Although these open-type devices can effectively be used for surface culture, they have a disadvantage that the culture is liable to contamination with airborne infectious microbes because of their open-type design. This problem is particularly significant in industrial operations and it has greatly limited the industrial application of surface culture.

To solve the problem, the prior art has so far provided several closed-type containers that may be used for surface culture. One of the closed-type containers is flexible culture bags made from flexible, thin plastic film which are either gas-permeable or non-permeable. Typically, culture bags are made from, at least in part, gas-permeable film for the purpose to facilitate air exchange between the inside and the outside of the bag. Examples of the gas-permeable culture bags are described in U.S. Pat. Nos. 4,939,151; 5,225,346; 5,686,304; and 5,736,398 for cell culture and in U.S. Pat. Nos. 4,311,477; 4,063,383; 4,977,702; and 5,659,997 for fungal culture. If culture bags are made from non-permeable film, the bags must equipped with venting filter devices to facilitate air change for aerobic growth.

In general, the flexible culture bags are considered more advantageous than rigid containers, because they use less solid materials and hence less solid waste for disposal, they can be sterilized by various methods such as irradiation, ethylene oxide, and autoclaving, and they take less space during storage and shipping. A major drawback of the flexible culture bags in consideration of surface culture, however, is that the bags have no self-support to stay inflated so that a stationary interface between a liquid medium and a gaseous phase can not be maintained. This is because the air sealed inside the bag is gradually forced out through either the gas-permeable wall or the venting filter of the bag under the pressure applied by the weight of the top web of the bag. As a result, the bag is gradually deflating until the top web of the bag touches the surface of the liquid medium and destroys the interface which is essential for surface culture. This drawback has practically made it impossible to use of flexible culture bags in surface culture at both laboratory and industrial scales.

To overcome the drawback, Kybal and Vlcek (A Simple Device for Stationary Cultivation of Microorganisms, Biotechnology and Bioengineering, Vol. 18, pp. 1713–1718, 1976) developed a surface culture system for using flexible culture bags equipped with an inlet tube and vent holes. When in use, the bag is placed on a stationary platform and inflated with sterile air that is continuously fed in through the inlet tube and vent out through the vent holes. The purposes of the continuous air flow are to maintain a headspace above the liquid medium so that the surface culture can occur and to facilitate air exchange and maintain an aerobic environment in the bag. Their system are further developed for submerged culture by placing the bag on a motion platform as described by Kybal and Sikyta (A Device for Cultivation of Plant and Animal Cells, Biotechnology Letters, Vol. 7, pp. 467–470, 1985) and by Singh in U.S. Pat No. 6,190,913.

Although the Kybal and Vlcek's system provides a closed, aerobic environment for surface culture, it requires continuous air flow to inflate the bag throughout the operation, which is often costly and complex to set up and operate. In addition, the air flow causes quicker evaporation of the liquid medium, which often result a significant lose of culture volume. To offset evaporation, the humidified air is required to feed through the bag, which makes the system even more complicate to operate and maintain.

To address the deficiency of flexible culture bags in surface culture and the above problems, the present invention provides a convenient, effective and reliable method for using flexible culture bags in surface culture.

BRIEF SUMMARY OF THE INVENTION

In accordance with the present invention, a method for using flexible bags for surface culture of microorganisms and cells and the devices upon which the method are practiced are disclosed. The method comprises the following steps: (a) introducing a growth medium and a culture sample into a culture bag; (b) inflating the bag with air to create a headspace; (c) sealing the bag; (d) placing the bag on a flat platform to spread out the growth medium; and (e) mounting an external support device on the top web of the bag to prevent the bag from deflating so that a stationary interface between the headspace and the growth medium is maintained invariably throughout the cultivation.

Accordingly, the present invention provides the following objects and advantages:

(a) to provide a convenient, effective and reliable method which enables the use of flexible culture bags for surface culture;

(b) to provide a method for surface culture in a closed, aerobic environment, and thus, to eliminate the need for the high cost, clean-room operation with open-type devices;

(c) to provide a method for easy and safe handling of flexible culture bags in surface culture operation;

(d) to provide a method for surface culture which can be implemented and scaled up easily and cost effectively at both laboratory and industrial scales; and (e) to provide a method for surface culture which produces minimum solid waste for disposal, in which all components except the bags are reusable.

Further objects and advantages will become apparent from a consideration of the ensuing description and drawings.

BRIEF DESCRIPTION OF THE DRAWINGS

FIG 1 is a top view showing the configuration of a flexible culture bag on a flat platform mounted with external self-support devices on the top web of the bag.

FIG. 2 is a cross-sectional view of the configuration shown in FIG. 1.

FIG. 3 is a top view showing the configuration of a flexible culture bag on a rigid tray mounted with external support cable on the top web of the bag.

FIG. 4 is a cross-sectional view of the configuration shown in FIG. 3.

FIG. 5 is a top view showing the configuration of a flexible culture bag in a rigid box frame where the lid of the box frame mounts on the top web of the bag.

FIG. 6 is a cross-sectional view of the configuration shown in FIG. 5.

DETAILED DESCRIPTION OF THE INVENTION

Figure 7:
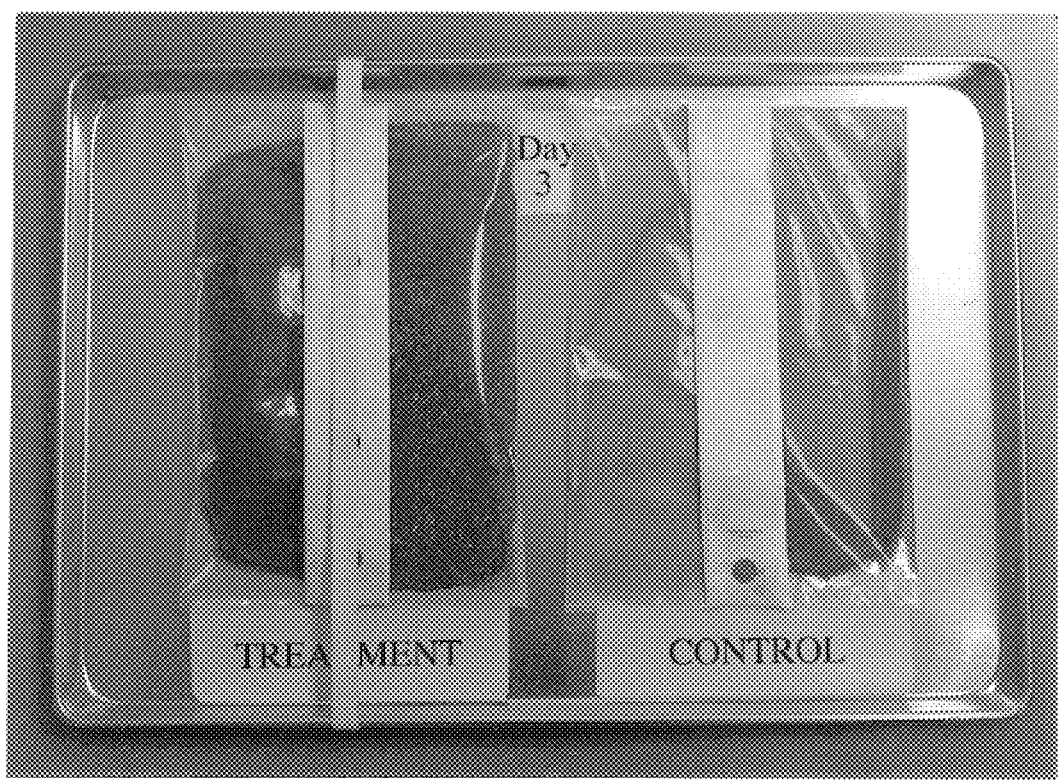
FIG. 7 is a photograph showing a surface culture experiment at day 3, where the control bag is deflated while the treatment bag remains inflated and shows healthy growth and sporulation.

Embodiments of the present invention address the deficiencies of flexible culture bags for surface culture where a stationary interface between a gaseous phase and a growth medium is essential. The embodiments provide external support assembly to prevent flexible culture bags from deflating and, thus, a sufficient headspace above the growth medium can be maintained throughout any length of cultivation period.

In a typical embodiment illustrated in FIGS. 1 and 2 (top and cross-sectional views, respectively), a flexible culture bag (8) that is filled with a predetermined volume of liquid growth medium (12) and sufficient amount of air or a gas mixture containing oxygen to create headspace (14) is placed on a platform (20). The platform (20) can be any structure with a flat, hard surface which allows the medium (12) to spread out horizontally and evenly to give the largest interface area possible between the surface of the medium (12) and the headspace (14). The interface is essential for surface culture of microorganisms and cells. The headspace (14) is maintained by an external support assemble comprising of at least one self-support, arch-shaped member (22) with double side adhesive tape strips (24) mounted on the upper surface of the top web (10) of the bag (8). Such a configuration prevent the bag (8) from deflating by keeping the top web of the bag in a fixed position. As a result, the headspace (14) is maintained invariably throughout the cultivation. When harvesting, the bag (8) can easily be removed from the configuration by simply detaching from the tape strips (24). Both the platform (20) and the external support assembly are reusable, and the flexible culture bag is the only solid waste created when using this invention.

The self-support, arch-shaped member (22) can be fabricated with rigid materials such as metal, wood, and plastics. The structure of the member can be as simple as a bent rod or as complex as an adjustable arm in both height and length to accommodate various sizes of culture bags.

The adhesive tape strips (24) are preferably double side adhesive tapes which form a strong bond on plastics but do not cause permanent sticking. One example of the tapes is Scotch® Double-Stick Tapes (3M, St. Paul, Minn.). Other mounting or fastening tapes such as Sticky Back® hook-loop fastener (Velcro USA Inc., Manchester, N.H.) can also be used.

In another embodiment illustrated in FIGS. 3 and 4 (top and cross-sectional views, respectively), the present invention provides an alternative method to facilitate easy handling of the bag in a surface culture operation. This object is achieved by using rigid, flat-bottom trays (40) and an external support assembly comprising of flexible elastic cables (44) which have clamping devices (46) at each end and hook-loop tape strips (48). When in use, one can simply place the flexible bag (8) prepared as described above on the tray (40), straiten the elastic cables (44) over the bag (8) on the edges (42) of the tray (40) by using the clamps (46), and mount the straitened cable on the upper surface of the top web (10) of the bag (8) by using hook/loop tape strips (48). The straitened cable is capable of holding the top web (12) of the bag (8) in a fixed position above the medium (12). In such configuration, not only the headspace (14) in the bag (8) is maintained, but also the bag on the tray can be easily handled, moved or stacked either manually or mechanically without demolishing the headspace in the bag.

In a further embodiment illustrated in FIGS. 5 and 6 (top and cross-sectional views, respectively), the present invention provides another secure method for safe handling of the bag in surface culture operation by using a rigid box frame instead of platform or trays. The box frame (60) has a hinged or removable lid (62) which allows for placing and retrieving the bag (8). The lid (62) has double side adhesive tape strips (64) on its under side. When in use, one can simply place the flexible bag (8) prepared as described above into the box frame (60), close the lid (62) over the bag (8) whereby the tape strips (64) adheres on the upper surface of the top web (10) of the bag (8). In such configuration, the headspace (14) in the bag (8) is maintained and the bag (8) is secured in the box frame (60) to prevent any accidental breakage or punctures of the bag during handling.

The box frame (60) is preferably made from rigid materials such cardboard, wood, plastics, or metal. Preferably, the box frame (60) has a flat bottom which is sufficiently large to accommodate the bag (8) and a plurality of holes and openings on the walls and the lid (62) of the box frame (60) to facilitate aeration.

The lid (62) of the box frame can be either removable or hinge joined and it can be securely closed by a lock device or other fastening means. The adhesive tape strips (64) are preferably double side adhesive tapes which form a strong bond on plastics but do not cause permanent sticking. An example of the tapes is Scotch® Double-Stick Tapes (3M, St. Paul, Minn.). Other mounting or fastening tapes such as Sticky Back® hook-loop Fastener (Velcro USA Inc., Manchester, N.H.) can also be used.

The following is an example that illustrates the basic concept of the present invention in practical use. To demonstrate the effectiveness of the present invention, the surface culture performed according to the present invention was conducted side by side with experimental control.

EXAMPLE 1

Materials and Methods

Sterile culture bags made from polyethylene film with a gas-permeable membrane strip on the top web were partially filled with 300 ml of sterile 2% malt extract broth. The bags were then inoculated with an antibiotics-producing strain Penicillum sp., filled with sterile air to create headspace, and sealed. The bags were placed on flat trays to allow the medium to spread out horizontally before an external support assembly was mounted on the top web of the bags. The assembly was an elastic VelStretch® (Velcro USA Inc.) cable (the loop side) straightened by clamping on the edges of the tray. The straightened cable was mounted on the bag by griping the hook side of Sticky Back® (Velcro USA Inc.) strips which were pre-fixed on the top web of the bags. An experimental control was conducted in tandem using an identical set of the culture bags that are prepared in the same manner as described above but without the use of an external support assembly.

Results

As shown in FIG. 7, the headspace in the treatment bags mounted with the external assembly maintained at least 2-cm headspace throughout the entire cultivation period. The microorganism grew rapidly and sporulated vigorously in the treatment bags. In contrast, the control bags as shown in FIG. 7, which did not have the external support, collapsed and lost its headspace within 24 hours. As a result, the interface between the headspace and the medium, which is essential for the surface culture, was destroyed and the microorganism grew poorly and unevenly in the control bags.

The invention has been described in an illustrative manner, and it is to be understood that its spirit and scope are not limited by the specific embodiments disclosed above.

I claim:

1. A method for culturing microorganisms and cells in a flexible culture bag, comprising the steps of:
   (a) introducing a growth medium and a culture sample into said bag;
   (b) introducing air into said bag in an amount sufficient to create a predetermined headspace above said growth medium;
   (c) sealing said bag;
   (d) placing said bag on a flat platform whereby said growth medium spreads out horizontally inside said bag and wherein said bag thus comprises a top surface; and
   (e) mounting an external support means for holding the top surface of said bag to prevent said bag from deflating,
   whereby said method permits the use of said flexible culture bag for culturing microorganisms and cells on a stationary interface between the headspace and the growth medium in said bag maintained by said external support means.

2. The method according to claim 1, wherein said bag is bags made from flexible, plastic sheets.

3. The method according to claim 1, wherein said support means is an assembly comprising at least one self-support, arch-shaped member with at least one attachment strip fixed on said member for attaching the top web of said bag to said member.

4. The method according to claim 3, wherein said attachment strip is a double side adhesive tape.

5. The method according to claim 3, wherein said attachment strip is one face of a hook and loop coupling tape whereas the corresponding face is mounted on said bag.

6. A method for culturing microorganisms and cells in a flexible culture bag, comprising the steps of:
   (a) introducing a growth medium and a culture sample into said bag;
   (b) introducing air into said bag in an amount sufficient to create a predetermined headspace above said growth medium;
   (c) sealing said bag;
   (d) placing said bag on a rigid tray whereby said growth medium spreads out horizontally inside said bag and wherein said bag thus comprises a top surface; and
   (e) mounting an external support means for holding the top surface of said bag to prevent said bag from deflating, whereby said method permits the use of said flexible culture bag for culturing microorganisms and cells on a stationary interface between the headspace and the growth medium in said bag maintained by said external support means.

7. The method according to claim 6, wherein said bag is made from flexible, plastic sheets.

8. The method according to claim 6, wherein said support means is an assembly comprising (a) at least one self-support member which has a length sufficient for mounting on the top edge of said tray and (b) at least one attachment strip fixed, on said member for attaching the top web of said bag to said member.

9. The method according to claim 6, wherein said support means is an assembly comprising (a) at least one flexible cable which becomes straighten when mounting on the edges of said tray by clamping devices at each end for mounting said cable and (b) at least one attachment strip fixed on said cable for attaching the top web of said bag to said cable.

10. The method according to claim 8, wherein said attachment strip is a double side adhesive tape.

11. The method according to claim 8, wherein said attachment strip is one face of a hook and loop coupling tape whereas the corresponding face is mounted on said bag.

12. The method according to claim 9, wherein said attachment strip is a double side adhesive tape.

13. The method according to claim 9, wherein said attachment strip is one face of a hook and loop coupling tape whereas the corresponding face is mounted on said bag.

14. A method for culturing microorganisms and cells in a flexible culture bag, comprising the steps of:
   (a) introducing a growth medium and a culture sample into said bag;
   (b) introducing air into said bag in an amount sufficient to create a predetermined headspace above said growth medium;
   (c) sealing said bag;
   (d) placing said bag on a box tray whereby said growth medium spreads out horizontally inside said bag and wherein said bag thus comprises a top surface; and
   (e) mounting the top surface of said bag to the inner surface of said box frame thereby providing external support means to prevent said bag from deflating,
   whereby said method permits the use of said flexible culture bag for culturing microorganisms and cells on a stationary interface between the headspace and the growth medium in said bag maintained by said external support means.

15. The method according to claim 14, wherein said bag is made from flexible, plastic sheets.

16. The method according to claim 14, wherein said bag is mounted to said box frame by adhesive.

17. The method according to claim 14, wherein said bag is mounted to said box frame by adhesive tapes.

18. The method according to claim 14, wherein said bag is mounted to said box frame by hook and loop coupling tapes.

* * * * *